United States Patent [19]
Eeckhout et al.

[11] Patent Number: 5,438,068
[45] Date of Patent: Aug. 1, 1995

[54] METHOD OF TREATING COLON DISTURBANCES WITH PHARMACEUTICAL COMPOSITIONS CONTAINING IMIDAZOL-1-YL COMPOUNDS

[75] Inventors: Christian Eeckhout, Bad Pyrmont; Ulf Preuschoff, Uelzen; Samuel David, Hanover, all of Germany

[73] Assignee: Kali-Chemie Pharma, Hanover, Germany

[21] Appl. No.: 145,164

[22] Filed: Nov. 3, 1993

[30] Foreign Application Priority Data

Nov. 14, 1992 [DE] Germany .................. 42 38 553.9

[51] Int. Cl.[6] .............................................. A61K 31/415
[52] U.S. Cl. ................................................... 514/397
[58] Field of Search ................................... 514/396, 397

[56] References Cited

U.S. PATENT DOCUMENTS 4,939,136  7/1990  Haeck et al. ............... 514/183

FOREIGN PATENT DOCUMENTS 201165  11/1986  European Pat. Off. .

OTHER PUBLICATIONS

Gore et al., Aliment. Pharmacol. Thera., vol. 4, pp 139–144 (1990).
Lamers, "Ondansetron: Effects on . . . ", Scand. J. Gastroenterol., vol. 188, 1991 supplement, pp. 124–126.
Miyata et al., J. Pharmacol. Exp. Thera., vol. 261, No. 1, pp. 297–303 (1992).
Steadman et al., Mayo Clin. Proc., vol. 67, No. 1, pp. 732–738 (1990).
Prior et al., GUT, vol. 31, No. 10, p. A1174 (1990).
Talley, Aliment. Pharmacol. Ther., vol. 6, No. 3 pp. 273–289 (1992).
Biosis Abstract of Alimentary Pharmacology and Therapeutics. 6(3) 1992. Talley.

Primary Examiner—Zohreh Fay
Attorney, Agent, or Firm—Evenson, McKeown, Edwards & Lenahan

[57] ABSTRACT

Use of imidazol-1-yl compounds of the general formula I

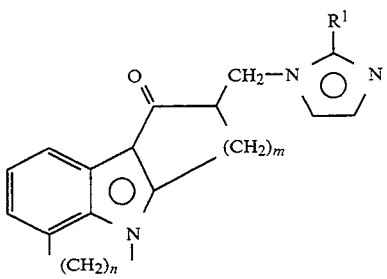

wherein
  $R^1$ denotes lower alkyl or hydrogen;
  m represents 2 or 3, and
  n represents 2 or 3;
or a physiologically acceptable acid addition salt thereof for treating functional disturbances of the lower intestinal tract in larger mammals and humans associated with increased pain sensitivity and/or anomalies in stool passage in the colon region.

11 Claims, No Drawings

METHOD OF TREATING COLON DISTURBANCES WITH PHARMACEUTICAL COMPOSITIONS CONTAINING IMIDAZOL-1-YL COMPOUNDS

BACKGROUND OF THE INVENTION

The present invention relates to the use of imidazol-1-yl compounds for the treatment of functional gastrointestinal disturbances in the region of the lower intestinal tract in a mammal and to the preparation of medicaments suitable for use in such a treatment.

SUMMARY OF THE INVENTION

The object of the present invention is to provide a method of treating functional disease symptoms in the region of the lower intestinal tract.

This and other objects of the invention are achieved by providing a method of treating a mammal suffering from a functional disturbance of its lower intestine associated with at least one symptom selected from the group consisting of increased pain sensitivity upon stool passage through the lower intestine and anomalies in stool passage through the lower intestine, said method comprising administering to said mammal an effective intestinal function promoting amount of an imidazol-1-yl compound corresponding to the formula I:

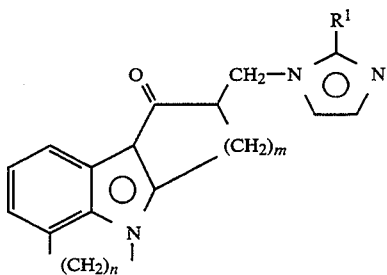

wherein
$R^1$ is hydrogen or a lower alkyl group containing 1 to 4 carbon atoms;
m is 2 or 3, and
n is 2 or 3,
or a physiologically acceptable acid addition salt thereof.

DETAILED DESCRIPTION OF PREFERRED EMBODIMENTS

According to the invention, imidazol-1-yl compounds of the general formula I

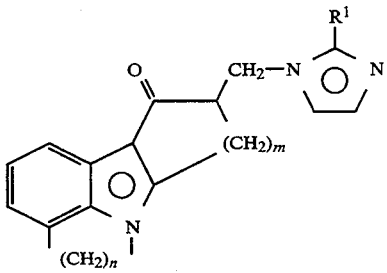

wherein
$R^1$ denotes lower alkyl or hydrogen,
m represents 2 or 3, and
n represents 2 or 3,
and physiologically acceptable acid addition salts thereof, are used for the preparation of pharmaceutical formulations for the treatment of functional disturbances of the lower intestinal tract associated with increased pain sensitivity and/or anomalies in stool passage in the colon region in larger mammals and humans.

In the compounds employed according to the invention, m preferably represents 2 and n preferably represents 3. $R^1$ preferably represents a lower alkyl group, which can be straight-chain or branched and can contain 1 to 4, in particular 1 to 2, carbon atoms, and is preferably methyl.

The compounds of the formula I have an asymmetric center at the point where the tetracyclic ring structure is connected to the imidazol-1-yl-methyl side chain, and this asymmetric center may be in the R- or S-configuration. The individual stereoisomeric forms of the compounds of the formula I or mixtures thereof can be used according to the invention.

5,6,9,10-tetrahydro-10-[(2-methyl-1H-imidazol-1-yl)-methyl]-4H-pyrido[3,2,1-jk]carbazol-11(8H)-ones, in particular (S)-5,6,9,10-tetrahydro-10-[(2-methyl-1H-imidazol-1-yl)-methyl]-4H-pyrido[3,2,1-jk]carbazol-11(8H)-one, and physiologically acceptable acid addition salts thereof have proved to be particularly suitable.

Suitable physiologically acceptable acid addition salts of the compounds of the formula I include salts with inorganic acids, for example hydrogen halide acids, in particular hydrochloric acid, or sulfuric acid, or with organic acids, for example lower aliphatic mono- or dicarboxylic acids, such as acetic acid, fumaric acid, tartaric acid, lactic acid, maleic acid or citric acid, or aromatic carboxylic acids, such as, for example, salicylic acid, dibenzoyltartaric acid or ditoluoyltartaric acid, or also sulfonic acids, such as, for example, lower alkylsulfonic acids, such as methanesulfonic acid, or benzenesulfonic acids which are optionally substituted in the benzene ring by halogen or lower alkyl, such as p-toluenesulfonic acid.

The compounds employed according to the invention for the treatment of functional disturbances of the lower intestinal tract fall within the scope of the compounds containing a fused indole structure which have 5-HT-antagonistic properties and are described in U.S. Pat. No. 4,939,136, and are known from this patent, the disclosure of which is incorporated herein by reference. The compounds of the formula I can be prepared in a known manner as described in the aforementioned U.S. Patent, or by analogous processes.

It has now been found, surprisingly, that the group of compounds of the formula I used according to the invention are not only suitable for the treatment of diseases in the gastroduodenal region of the stomach and the duodenum, that is to say for the treatment of dyspepsias and emeses, as stated in the aforementioned U.S. Pat. No. 4,939,136, but also can be used to treat diseases and functional disturbances of the lower intestinal tract.

This results unexpectedly in possibilities for the treatment of completely different diseases which are not related to dyspeptic states.

Disturbances in the region of the distal small intestine and increased pain sensitivity with physiological, digestion-related dilations of the colon can lead to motility disturbances, such as are observed with so-called "irritable bowel syndrome" (=IBS). The accompanying symptoms may also include disturbances in bowel movement, in particular abnormally accelerated passage of the stool in the colon, in addition to visceral pain and motility disturbances in the lower intestinal region.

It has now been found that the compounds of the formula I reduce the visceral pain sensitivity and can thereby prevent inhibition of colon motility caused by an over-sensitive reaction to colon dilation. The compounds additionally have a delaying action on stool passage through the colon, whereby they can normalize an abnormally accelerated colon passage.

The pharmacological actions of the compounds of the formula I in the region of the lower intestinal tract can be demonstrated in standard pharmacological tests on animals.

Description of the pharmacological test methods

I. Investigation of the action of the compounds on stool passage through the colon in rats.

The average residence time in the colon of radioactively labelled material introduced thereinto until it is excreted in the faeces was determined as a measure of the colon motility leading to stool excretion.

Groups of 8 male Wistar rats each were employed for the tests. Under ketamine anaesthesia, a small polyethylene catheter was inserted into the animals from the nape of the neck into the abdominal cavity and from there was inserted into the lumen of the proximal colon 2 cm away from the opening of the coecum into the proximal colon.

The animals were each injected with 0.1 ml of a $^{51}Cr$ radioactively labelled sodium chromate solution (=10 $\mu$ $^{51}Cr$/ml) through the catheter. Samples of the faeces excreted were then collected at 1 hour intervals until no further radioactivity was detectable in the faeces. The radioactivity contained in the faeces samples was measured with the aid of a gamma counter, and the average residence time of the radioactively labelled material in the colon was calculated from these measurements. This average residence time can serve as a measure of the rate of colon passage.

In a control group of animals, the average residence time of the $^{51}Cr$-labelled material in the colon was 7.1 hours. Subcutaneous administration of (S)-5,6,9,10-tetrahydro-10-[(2-methyl-1H-imidazol-1-yl)-methyl]-4H-pyrido3,2,1-jk]carbazol-11(8H)-one hydrochloride in a dose of 1 mg/kg 15 minutes before administration of the radioactively labelled sodium chromate caused a slowing down in the excretion from the colon and led to an increase in the average residence time of the radioactively labelled material in the colon to 9.8 hours. This shows that the test substance reduces the colon activity leading to the excretion of faeces.

II. Investigation of the influence of the compounds on visceral sensitivity in rats.

Male Wistar rats having a body weight of 250 to 350 g were prepared for electromyography by surgical treatment to implant electrodes of nickel/chromium wire into the wall of the proximal colon of each animal. Electromyographic recordings of colon movements were started 5 days after the surgeries. To carry out the tests, an inflatable balloon was introduced rectally into the colon of the animals until the end of the balloon was 1 cm away from the rectum, and the balloon was fixed to the tail in this position. During the test, the animals were kept in a tunnel-shaped cage in which they could move but could not turn around or run out. The colon motility was reduced by inflating the balloon to a diameter of 11 mm. In a group of control animals, this reduced the number of contraction series per 5 minutes to 43% of the original value. After ip administration of (S)-5,6,9,10 - tetrahydro -10-[(2-methyl-1H-imidazol-1-yl)-methyl]4H-pyrido[3,2,1- jk]carbazol- 11(8H) -one hydrochloride in a dose of 1 mg/kg before the start of the test, the sensitivity to dilation was reduced and the number of contraction series per 5 minutes was reduced only to 85% of the original value.

The foregoing pharmacological test results show that the compounds of formula I can hinder the disturbances in colon motility caused by stimulation of the afferent nerves and are therefore suitable for the treatment of IBS. The doses to be used can differ between individuals and of course will vary according to the nature of the condition to be treated and the identity of the active substance used. In general, however, suitable pharmaceutical dosage forms for administration to humans and larger mammals will contain 0.1 to 80 mg of active compound per individual dose, in particular 1 to 10 mg of active compound per individual dose.

In accordance with the invention, the active compounds can be contained in solid or liquid pharmaceutical formulations together with customary pharmaceutical carriers and/or adjuvants. Examples of solid preparations which may be mentioned include suppositories and orally administrable preparations, such as tablets, coated tablets, capsules, powders or granules. These preparations may contain known inorganic and/or organic pharmaceutical carriers and/or diluents, such as, for example, talc, lactose or starch, in addition to conventional pharmaceutical adjuvants, for example lubricants or tablet disintegrating agents. Liquid preparations, such as suspensions or emulsions of the active compounds, may contain the customary diluents, such as water and oils, and/or suspending agents, such as polyethylene glycols and the like. Other adjuvants may additionally be added, such as, for example, preservatives, flavor improvers or enhancers, and the like.

The active compounds can be mixed and formulated with the pharmaceutical carriers and/or adjuvants in a known manner. In order to prepare solid medicament forms, for example, the active compounds can be mixed with the carrier and/or adjuvants in a conventional manner and the mixture can be granulated in the wet or dry state. The granules or powder of the resulting mixture can be introduced directly into capsules or pressed in a conventional manner into tablet cores, and if desired, the tablet cores can be coated in a known manner.

The following examples are intended to illustrate the preparation of pharmaceutical formulations containing compounds of the formula I in further detail, without, however, limiting the scope of the invention.

| Composition: | |
|---|---|
| (S)-5,6,9,10-tetrahydro-10-[(2-methyl-1H-imidazol-1-yl)-methyl]-4H-pyrido[3,2,1-jk]-carbazol-11(8H)-one hydrochloride | 5 parts |
| Maize starch | 30 parts |
| Lactose | 70 parts |
| Kollidon 25 TM | 5 parts |
| Magnesium stearate | 2 parts |
| Talc | 3 parts |
| Total | 115 parts |

Preparation instructions

The active compound was mixed with the maize starch and finely powdered lactose in a mixer. The resulting mixture was moistened thoroughly with a 20% solution of polyvinylpyrrolidone (Kollidon 25 ™ from BASF) demineralized water. Optionally, further demineralized water was added to assure a desired consistency. The moist granules were passed through a 2 mm sieve, dried on trays at 40° C. and then passed through a 1 mm sieve (Frewitt machine). After the granules had been mixed with magnesium stearate and talc, tablets weighing 115 mg were pressed from the mixture, so that each tablet contained 5 mg of the active compound.

Example 2: Capsules

| Composition: | |
|---|---|
| (S)-5,6,9,10-tetrahydro-10-[(2-methyl-1H-imidazol-1-yl)-methyl]-4H-pyrido[3,2,1-jk]-carbazol-11(8H)-one hydrochloride | 5 parts |
| Maize starch | 20 parts |
| Lactose | 60 parts |
| Kollidon 25 ™ | 3 parts |
| Magnesium stearate | 1.5 parts |
| Aerosil 200 ™ | 0.5 parts |
| Total | 90 parts |

Preparation of capsules

The active compound was mixed with the maize starch and finely powdered lactose in a mixer. The resulting mixture was moistened thoroughly with a 20% solution of polyvinylpyrrolidone (Kollidon 25 ™ from BASF) in demineralized water. Optionally, additional demineralized water was added to obtain a desired consistency. The moist granules were passed through a 1.6 mm sieve (Frewitt machine), dried on trays at 40° C. and then passed through a 1 mm sieve (Frewitt). After the granules had been mixed with magnesium stearate and highly disperse silicic acid (Aerosil 200 ™, Degussa), 90 mg portions thereof were introduced by means of an automatic capsule machine into size 4 hard gelatin capsules, so that each capsule contained 5 mg of the active compound.

The foregoing description and examples have been set forth merely to illustrate the invention and are not intended- to be limiting. Since modifications of the disclosed embodiments incorporating the spirit and substance of the invention may occur to persons skilled in the art, the invention should be construed to include everything within the scope of the appended claims and equivalents thereof.

What is claimed is:

1. A method of treating a mammal suffering from a functional disturbance of its lower intestine associated with increased pain sensitivity upon stool passage through the lower intestine and/or anomalies in stool passage through the lower intestine, said method comprising administering to said mammal an effective intestinal function promoting amount of an imidazol-1-yl compound corresponding to the formula I:

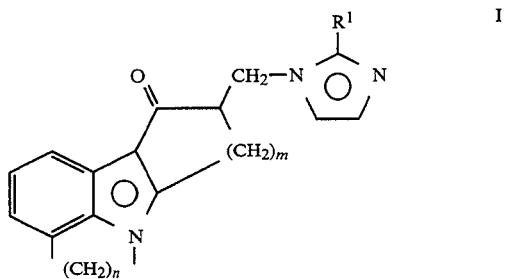

wherein
   $R^1$ is hydrogen or a lower alkyl group containing 1 to 4 carbon atoms;
   m is 2 or 3, and
   n is 2 or 3,
or a physiologically acceptable acid addition salt thereof.

2. A method according to claim 1, wherein said functional disturbance of the lower intestine is a disturbance associated with increased pain sensitivity upon stool passage through the lower intestine.

3. A method according to claim 1, wherein said functional disturbance of the lower intestine is a disturbance associated with an anomaly in stool passage through the lower intestine.

4. A method according to claim 1, wherein m is 2 and n is 3.

5. A method according to claim 4, wherein said compound is 5,6,9,10-tetrahydro-10-[(2-methyl-1H-imidazol-1-yl)-methyl]-4H-pyrido[3,2,1-jk]carbazol-il(8H)-one or a pharmaceutically acceptable acid addition salt thereof.

6. A method according to claim 5, wherein said compound is (S)-5,6,9,10-tetrahydro-10-[(2-methyl-1H-imidazol-1-yl)-methyl]-4H-pyrido[3,2,1-jk]carbazol-11(8H)-one or a physiologically acceptable acid addition salt thereof.

7. A method according to claim 1, wherein said compound is administered in combination with a conventional pharmaceutical carrier or adjuvant.

8. A method according to claim 1, wherein said compound is administered in a unit dose containing from 0.1 to 80 mg of said compound.

9. A method according to claim 6, wherein said compound is administered in a unit dose containing from 1 to 10 mg of said compound.

10. A method according to claim 1, wherein said functional disturbance of the lower intestine is irritable bowel syndrome.

11. A method according to claim 1, wherein said functional disturbance of the lower intestine is abnormally accelerated passage of stool through the lower intestine.

* * * * *